May 29, 1973 R. S. MOORE Plant Pat. 3,346
MINIATURE ROSE PLANT
Filed Sept. 7, 1971
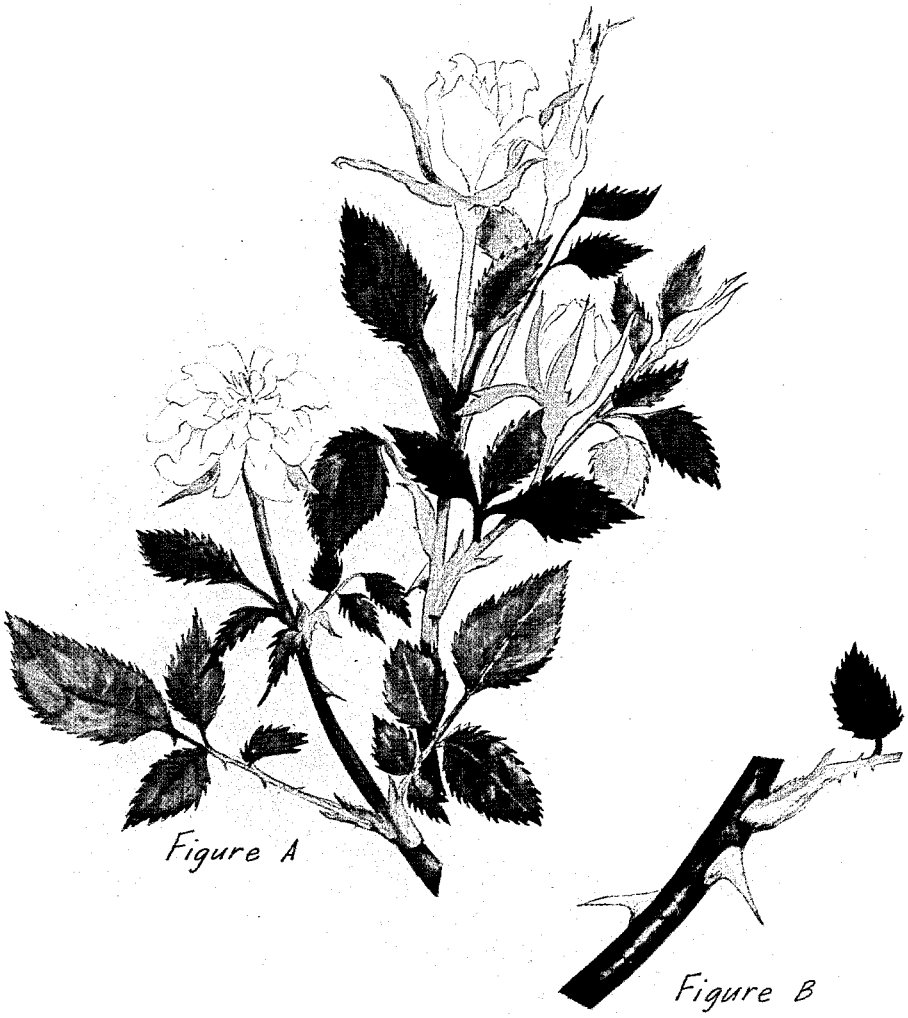
WITNESS
Jeanette Nunn Copley
INVENTOR
Ralph S. Moore

United States Patent Office

Plant Pat. 3,346
Patented May 29, 1973

3,346

MINIATURE ROSE PLANT

Ralph S. Moore, 2519 E. Noble Ave.,
Visalia, Calif. 93277

Filed Sept. 7, 1971, Ser. No. 178,514
Int. Cl. A01h *5/00*
U.S. Cl. Plt.—7 1 Claim The present invention relates to a new and distinct variety of hardy, dwarf, bush type rose of the miniature class; the variety being primarily characterized—as to novelty—by bright orange to orange-pink buds and flowers which in general color effect is an all over shade or blend of orange to orange-pink color (in varying shades) from the bud stage to the finished flower.

The variety is further characterized by:

Well shaped buds of hybrid tea rose form.

Considerable fragrance (fruit—nectarine).

An abundance of bloom, with flowers borne singly and in loose clusters.

A plant which is vigorous, of rounded spreading shape and with normal green, semi-glossy small foliage with pointed leaflets; the bud and flower being similar in size and form to the variety "Yellow Doll" (U.S. Plant Patent No. 2,450). The plant which has a normal average height of 10 to 14" at maturity can easily be maintained at a lower height with occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, California, under conditions careful control and observation, as a cross between "Little Darling" (floribunda) (U.S. Plant Patent No. 1,581—expired), as the seed parent, and "Fairy Princess," climbing miniature (not patented), as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identification being by reference to the British Colour Council Horticultural Colour Chart, except where common terms of color definition are employed.

Type: Hardy; dwarf; bush; seedling; greenhhouse; outdoors; cut flowers; garden decoration; potted plant.

Class: Miniature.

Flowers: Continuity—intermittent to continuous throughout season.

Fragrance: Quite fragrant; fruity (nectarine).
Lasting quality—very good.

Flowers borne: Singly and several together, on medium length slender wiry stems.

Quantity of bloom: Average both outside and in greenhouse.

Bud: Peduncle—medium to long; slender; erect; light green; smooth.

*Before calyx breaks.*—Size—small. Form: Pointed; with foliaceous appendages on surface of bud and foliaceous parts extending beyond tip of bud equal to one half or more of its length. Color: Medium green.

*As calyx breaks.*—Size—small. Form: Medium length, long pointed. Color: Orange to red-orange. (Yellow at base then blended and/or overlaid with Scarlet 19 on upper two thirds of petal.) Opening: Opens well in all weather.

Bloom: Size when fully open; small, about 1¼ to 1½". Petalage: Double—40 to 50 petals (sometimes more); petals arranged regularly. Sometimes additional petaloids. Form: Flat or slightly high centered at first; later at maturity becoming rounded with petals reflexing outward and downward; flower often becoming somewhat ball-shaped.

Petals: Satiny both inside and outside. Shape: Outside petals broad lanceolate (sometimes with acute tip); edges tend to fold back to give petals a pointed effect; intermediate—same as above. Color: Newly opened flower from plant grown indoors (lightly shaded plastic house) August 1971, Visalia, Calif.:

*Outside petal.*—Outside surface—Azalea Pink 618 blending to yellow at base; inside surface—Mandarin Red 17/2, shading and blending into yellow toward base; base—yellow.

*Intermediate petal.*—Outside surface—Mandarin Red 17/1 shading and blending into yellow at base; inside surface—yellow at base, overlaid and blended with Mandarin Red 17/1 on upper one half of petal.

*Inside petal.*—Similar to intermediate petal. General color effect newly opened flower—orange. Three days open—becomes lighter to orange-pink shade or blend of pink and orange. Behaviour—old flowers may hang on for a time then drop from plant at base of pedicel. Flower longevity (August 1971, in greenhouse) 4 to 5 days or longer.

Reproductive organs:

*Stamens.*—Moderate number to none; arranged regularly about pistil.

*Filaments.*—May vary in length; average; medium.

*Anthers.*—Well formed, yellow.

*Pollen.*—Little or none.

*Pistils.*—Average length and number.

*Styles.*—Medium length; bunched; pale green to near white.

*Stigma.*—Pale green or yellowish.

*Ovaries.*—All enclosed in calyx.

*Hips.*—None.

*Sepals.*—Permanent; spear shaped.

*Seeds.*—None.

Foliage:

*Leaves.*—Compound of five leaflets (occasionally 3 or 7); abundant; small; semi-glossy.

*Leaflets.*—Shape—lanceolate, apex acute; base rounded; margin serrate. Color—medium green. New growth and foliage often tinted red. Rachis—medium strength; upper side grooved; under side few thorns.

*Stipules.*—Long; narrow; medium long points, turning out at an angle of 45 degrees or more.

Growth:

*Habit.*—Dwarf; bushy; spreading; much branched.

*Growth.*—Free; vigorous.

*Canes.*—Medium; slender.

*Main stems.*—Color—medium green. Thorns—few thorns; slender; medium length, nearly straight or hooked slightly downward with sharp points; color—light to medium gray-brown.

*Branches.*—Color—medium green. Thorns—few or none; medium length; straight or hooked slightly downward; sharp points.

*New Shoots.*—Color—medium green. Thorns—few or none; medium length; straight or hooked slightly downward; sharp points; base oval; color—light green, often tinted pinkish. Prickles—none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by resemblance to the "Yellow Doll" miniature rose (U.S. Plant Patent No. 2,450) in general form of bud and flower but with color more orange than yellow, the general color effect of the freshly opened flower being an all over shade or blend of orange; and further characterized by a plant which is vigorous and compact in growth, easy to propagate by budding and from cuttings; with small medium green foliage, an abundance of bloom borne almost continuously throughout the growing season with flowers borne singly and in loose clusters.

No reference cited.

ROBERT E. BAGWILL, Primary Examiner